United States Patent [19]
Herold et al.

[11] Patent Number: 5,199,229
[45] Date of Patent: Apr. 6, 1993

[54] SAND BLASTING DEVICE

[75] Inventors: Wolf-Dietrich Herold, Seefeld; Peter Koran, Weilheim; Rudolf Haas, Unterbrunn, all of Fed. Rep. of Germany

[73] Assignee: THERA Patent GmbH & Co., KG Gesellschaft Fur Industrielle Schutzrechte, Seefeld, Fed. Rep. of Germany

[21] Appl. No.: 660,608

[22] Filed: Feb. 26, 1991

[30] Foreign Application Priority Data

Feb. 26, 1990 [DE] Fed. Rep. of Germany ... 9002268[U]

[51] Int. Cl.$^5$ .................. B24C 5/04; A61C 3/025
[52] U.S. Cl. ........................... 51/439; 51/426; 51/427; 433/88; 433/116; 433/125
[58] Field of Search ................ 51/317, 319–321, 51/424, 426, 427, 436, 438, 439; 433/83–85, 88, 114, 115, 116, 125, 166

[56] References Cited

U.S. PATENT DOCUMENTS

| 992,144 | 5/1911 | Babcock | 51/436 X |
|---|---|---|---|
| 2,400,912 | 5/1946 | Britt et al. | 433/125 X |
| 4,286,950 | 9/1981 | Hawk | 433/116 |
| 4,424,036 | 1/1984 | Lokken | 433/116 |
| 4,475,370 | 10/1984 | Stark et al. | 51/426 X |
| 4,540,365 | 9/1985 | Nelson et al. | 433/88 |
| 4,608,018 | 8/1986 | Ghedini et al. | 433/88 |
| 4,674,239 | 6/1987 | Jodoin | 51/427 X |
| 4,696,645 | 9/1987 | Saupe et al. | 433/125 |
| 4,776,794 | 10/1988 | Meller | |

FOREIGN PATENT DOCUMENTS

3727441A1 3/1980 Fed. Rep. of Germany.
3634700A1 4/1988 Fed. Rep. of Germany.

Primary Examiner—Bruce M. Kisliuk
Assistant Examiner—John A. Marlott
Attorney, Agent, or Firm—Foley & Lardner

[57] ABSTRACT

A hand-held sand blasting device, which is particularly useful for treating small surface areas, such as tooth faces in situ, includes a sand cartridge 20 adapted to be placed in a handle portion 10 of the device and rewardly sealed by a piston 34 which is adapted to be advanced by pressurized air. Part of the pressurized air flows along a longitudinal groove 25 formed in a wall of the handle portion 10 externally of the cartridge 20 and enters the cartridge through an opening 27 provided at a front portion thereof, where the relatively large cross-section of the main portion of the cartridge converges to the substantially smaller cross-section of a feed channel 28. The fine sand 21 is thus fluidized in this area and maintained flowable. Through the feed channel 28, the sand is supplied to a mixing chamber 30 where it is mixed with pressurized air and discharged through a nozzle pipe 33.

7 Claims, 1 Drawing Sheet

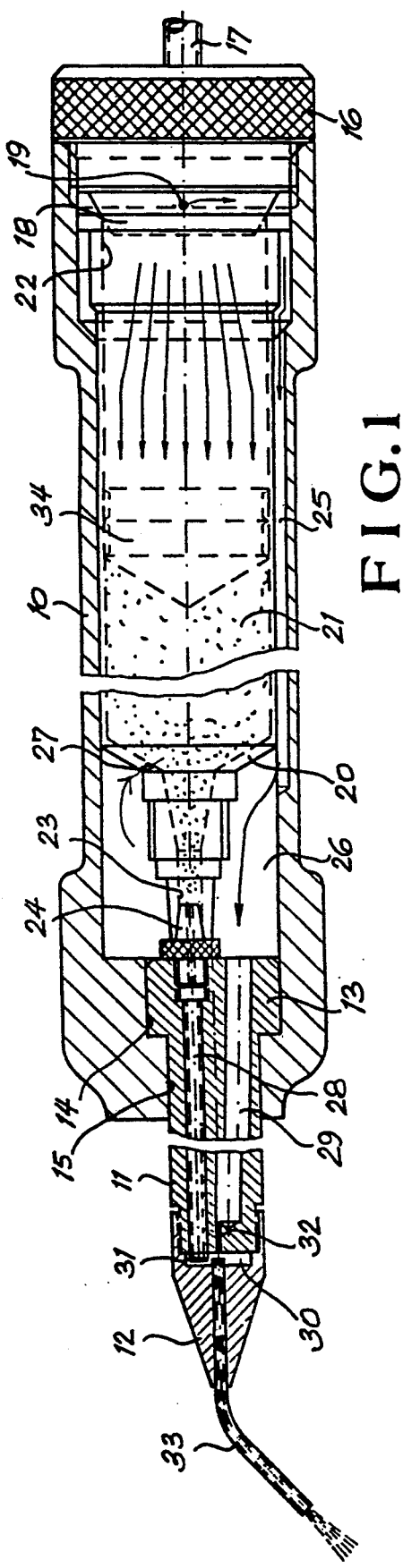
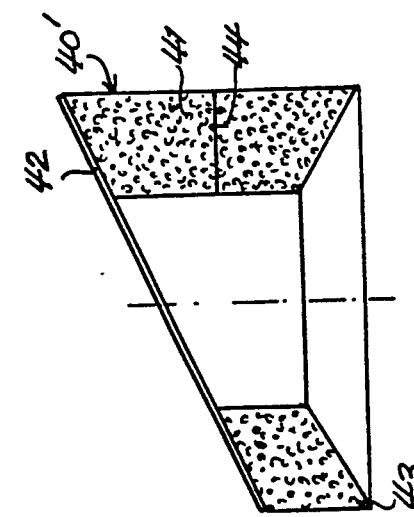
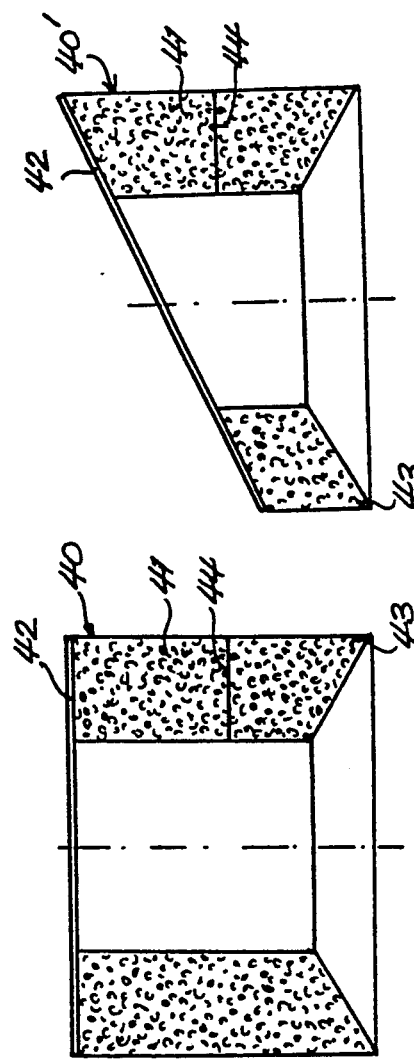
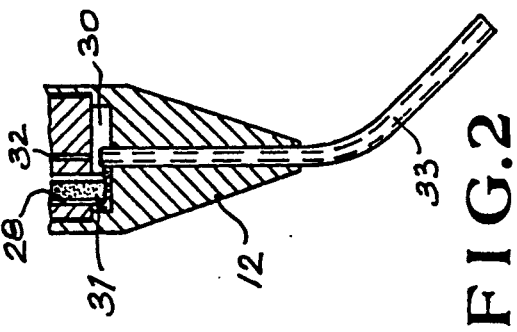

SAND BLASTING DEVICE

BACKGROUND OF THE INVENTION

This invention relates to a hand-held device for treating small surface areas, specifically tooth faces in a patient's mouth, with a jet of pressurized air containing particles of an abrasive material.

A device of this kind is known from U.S. Pat. No. 4,776,794, which employs an abrasive liquid. The known device cannot be operated with sand, powder or a powdery mixture as is required for producing a highly efficient abrasive jet.

DE-A1-3,727,441 describes a dental sand blasting apparatus with a stationary portion including a vibrator operated by pressurized air for preparing a sand-air mixture. The mixture is supplied via a hose to a discharge nozzle formed on a hand-held part. The overall apparatus is expensive and bulky.

Another sand blasting device is shown in DE-A1-3,634,700 wherein a sand container is rigidly connected with a nozzle head and the sand is sucked from the container by jet action exerted on the upper end of a downtake. In operation of this device, care must be taken that the downtake is always submerged by the sand. Therefore, the device may not be held in any desired orientation and is therefore not readily suited for treating surface areas which are difficult to access, such as locations in a patient's mouth. Moreover, the downtake requires a certain minimum cross-section for sucking the sand and is therefore unsuited to produce a very fine sand-blasting jet for treating minute surface areas, such as faces of a tooth.

SUMMARY OF THE INVENTION

It is an object of the invention to provide a sand blasting device which may be designed as an easy to handle and inexpensive hand-held instrument.

It is another object of the invention to provide a hand-held sand blasting device which can be operated irrespective of its orientation.

A further object of the invention resides in a device that permits sand-blasting of very small surface areas.

In view of these objects, the invention provides a hand-held device for treating small surface areas with a pressurized air jet containing sand particles, the device comprising: a compartment for holding a supply of sand; a piston rearwardly confining the compartment and adapted to be advanced by pressurized air; a feed channel communicating with the front end of the compartment; an opening provided in a wall of the compartment in the region where it communicates with the feed channel, for admitting pressurized air into said compartment for fluidizing the sand; a head portion including a mixing chamber for mixing the sand supplied through the feed channel with pressurized air; and a nozzle for blasting the mixture onto the surface area to be treated.

The fluidization of the sand ensures the proper operation of the device even with a very small cross-section of the feed channel, as is required to produce a correspondingly fine blasting jet. At the same time, advancement of the piston by the pressurized air renders the hand-held instrument operative irrespective of its orientation.

In a preferred embodiment of the invention, the device includes a handle portion defining a cylindrical inner space, and said compartment is formed as a replaceable cartridge adapted to be inserted into said cylindrical space. The device may thus be re-filled in a simple and clean manner.

In another preferred embodiment, the handle portion is provided with a pressurized-air connection, and a longitudinal channel is formed in a wall of the handle portion for supplying the pressurized air from said connection to the inlet opening and the mixing chamber. The pressurized air supplied at the rear end of the hand instrument is utilized for simultaneously advancing the piston, fluidizing the sand at the front end of the compartment, and forming the sand-blasting jet proper.

In a further embodiment, the head portion forming said mixing chamber and including the nozzle is detachably connected to a main portion of the device. This is of advantage because the chamber in which the sand is mixed with the pressurized air jet, and the nozzle pipe by which the mixed jet is discharged at high speed, are exposed to increased wear.

Another embodiment, in which the nozzle and the feed channel extend into the mixing chamber from opposite ends, are laterally displaced from each other and overlap each other, results in a labyrinth-type sealing which prevents sand from escaping from the compartment via the mixing chamber and the nozzle pipe when the pressurized air is switched off and the device is held with the nozzle down.

The invention further provides a sealing cup of air-permeable filter material and having an edge portion adapted to form an enclosure around the area to be treated, a window pane opposite said edge portion, and a peripheral wall with a passage for passing a front portion of said sand blasting device into said enclosure. This sealing cap serves to protect the environment against the extremely fine abrasive powder that may be used in the device according to the invention.

Further preferred embodiments relate to a particularly useful and inexpensive filter material, a preferred structure for achieving an efficient seal of the location being treated, which may be an area in a patient's mouth, and a useful design which permits easy observation of the location while under treatment.

BRIEF DESCRIPTION OF THE DRAWINGS

FIG. 1 is a longitudinal section through a sand blasting device according to an embodiment of the invention.

FIG. 2 shows the front portion of the device of FIG. 1 on an enlarged scale and in a position rotated by 90°.

FIG. 3 is a longitudinal section through a sealing cup for the location of treatment, which may be used in connection with the device of FIG. 1.

FIG. 4 is a view similar to FIG. 3 of a sealing cup according to an alternative embodiment.

DETAILED DESCRIPTION OF PREFERRED EMBODIMENTS

The sand blasting device shown in FIG. 1 includes three main portions: a handle portion 10, an intermediate portion 11, and a nozzle head 12. The intermediate portion 11 has a flange 13 which rests in a recess 14 provided in the front part of the handle portion 10, and a main part of reduced diameter which extends through a bore 15 communicating with the recess 14. The nozzle head 12 is screwed onto the front end of the intermediate portion 11.

The handle portion 10 is shaped as a hollow cylinder closed at its rear end by a screw 16. The screw 16 is provided with a hose connecting piece 17 for supplying pressurized air. The connecting piece 17 communicates with an outlet nozzle 18 of large cross-section which in turn opens towards the interior of the handle portion 10 and has a tapering outer surface and a transverse bore 19 extending through its sidewall.

FIG. 1 shows a cartridge 20 inserted into the hollow cylindrical interior of the handle portion 10 and containing an abrasive material 21 consisting of a very fine sand or powder. A rear opening 22 of the cartridge 20 rests on the conical outer surface of the outlet nozzle 18. At the front end of the cartridge 20, a tip portion with a slightly outwardly tapering outlet opening 23 is formed which rests on a correspondingly conically shaped outer surface of an inlet piece 24 of the intermediate portion 11. After the cartridge 20 has been inserted into the handle portion 10, the screw 16 is tightened until the cartridge is tightly clamped between the conical surface of the outlet nozzle 18 of the screw 16 and the conical surface of the inlet piece 24 of the intermediate portion 11.

A longitudinal groove 25 is provided in the cylindrical inner wall of the handle portion 10 and extends the entire length of the cylindrical main part of the cartridge 20 to form a flow path for pressurized air from the transverse bore 19 in the nozzle 18 to a chamber 26 formed at the front end of the interior space of the handle portion 10. In the region where the comparatively large cross-section of the cylindrical main part of the cartridge 20 narrows down to the substantially smaller cross-section of the outlet opening 23, the cartridge wall is provided with an opening 27 for admitting the pressurized air from the chamber 26 to the interior of the cartridge 20 to fluidize the sand in this area.

Two channels 28 and 29 extend longitudinally through the intermediate portion 11. The channel 28 serves to supply the sand from the inlet piece 24 to a mixing chamber 30 formed between the front surface of the intermediate portion 11 and the nozzle head 12. The other channel 29 serves for supplying the pressurized air from the chamber 26 to the mixing chamber 30. The front end of the sand supply channel 28 forms a projecting piece 31 extending beyond the front surface of the intermediate portion 11 into the mixing chamber 30. The front end of the pressurized-air channel 29 communicates with the mixing chamber 30 through a narrow jet channel 32.

A curved nozzle pipe 33 is fitted in the nozzle head 12 and has its rear end extending into the mixing chamber 30 coaxially with the jet channel 32. The projecting piece 31 of the sand supply channel 28 and the rear end of the nozzle pipe 33 are thus laterally displaced with respect to each other and extend into the mixing chamber 30 from opposite sides and to such an extent that they overlap in the direction of flow. This configuration results in a "labyrinth seal" as explained further below.

When pressurized air is supplied to the device, this air will flow through the outlet nozzle 18 against a piston 34 sealing the rear end of the cartridge 20 and press the sand 21 towards the outlet opening 23. Part of the air flows the transverse bore 19 and the longitudinal groove 25 along the outer side of the cartridge 20 and enters the chamber 26 where again a part of the pressurized air will flow through the opening 27 into the cartridge 20. The sand is thus fluidized and will remain flowable even in the small cross-section of the outlet opening 23 and that of the supply channel 28 extending through the intermediate portion 11, to enter the mixing chamber 30 through the projecting piece 31.

From the intermediate chamber 26, the pressurized air flows through the channel 29 and the jet channel 32 of the intermediate portion 11 also into the mixing chamber 30 where a vacuum is created by the enlargement of the cross-section at the end of the jet channel 32. This vacuum draws the sand into the air flow, and the mixture thus formed enters the nozzle pipe 33 in which the sand is accelerated to the final velocity of the air and is discharged as a sand-air mixture.

When the air is switched off and the device is held in the orientation shown in FIG. 2, i.e. with the nozzle extending downwardly, it would be principally possible for the sand to continue flowing and escape via the nozzle pipe. This is prevented by the labyrinth-type arrangement of the mixing chamber 30 referred to above. In the orientation shown in FIG. 2, when the mixing chamber 30 is filled with sand to such a level that the lower and of the projecting piece 31 is closed, this sand layer forms a barrier against further in-flow. At this filling level of the mixing chamber 30, however, the upper inlet end of the nozzle pipe 33 is not reached, so that any sand is prevented from escaping through the nozzle pipe 33.

As an alternative to supplying pressurized air to the sand blasting device via a hose fitted on the connecting piece 17 as described above, a propellant gas cartridge may be used, which may be rigidly connected to the handle portion 10 or may be adapted to be inserted into the handle portion 10 in addition to the sand cartridge 20. In this case, the device becomes entirely independent of a stationary air compressor and is thus completely freely movable.

The sealing cup 40 shown in FIG. 3 consists of a ring 41 of foamed plastics with a window pane 42 of clear synthetic material adhered on its end face. The cup edge 43 remote from the window 42 is bevelled and may thus be sealingly pressed onto uneven surfaces. A cut 44 extends through the peripheral wall of the ring 41. The front portion of the device shown in FIG. 1, i.e. the nozzle pipe 33, the tapering nozzle head 12 and, as far as necessary, the intermediate portion 11 may be passed through the cut 44 in order to place the front end of the nozzle pipe 33 at the required small spacing from the location of treatment. In case a tooth face is to be treated in situ, the sealing cup 40 is placed around the patient's mouth to protect the environment against the very fine powdery abrasive material, while the patient's throat is covered by a cofferdam.

The foamed synthetic material used for the sealing cup 40 acts as a filter through which the excessive air is purified and passed to the outside. In addition to the cut 44, a further, similar passage (not shown in FIG. 3) may be provided to pass an exhauster into the interior of the "sand blast chamber" formed by the sealing cup 40.

In the modified embodiment of FIG. 4, the sealing cup 40' differs from the one shown in FIG. 3 in that the window pane 42 extends at an angle with respect to the plane formed by the edge 43, which is advantageous for certain applications.

What is claimed is:

1. A hand-held device for treating small surface areas with a jet of pressurized air containing sand particles, comprising
a compartment for holding a supply of said sand,
a piston rearwardly confining said compartment and adapted to be advanced by pressurized air, a feed channel communicating with the front end of said compartment, an inlet opening provided in a wall of said compartment in a region where it communicates with said feed channel, for admitting pressurized air into the compartment for fluidizing the sand, a head portion including a mixing chamber for mixing the sand supplied through said feed channel with pressurized air, a nozzle for blasting the mixture onto the surface area to be treated, and a sealing cup of air-permeable foamed plastics filter material and having an edge portion adapted to form an enclosure around an area to be treated, a window pane opposite said edge portion, and a peripheral wall with a passage for passing a front portion of said nozzle into said enclosure.

2. The device of claim 1, wherein said edge portion is bevelled.

3. The device of claim 1, wherein said window pane extends at an angle with respect to a plane formed by said edge portion.

4. A hand-held device for treating small surface areas with a jet of pressurized air containing sand particles, comprising a nozzle for blasting said jet onto the surface area to be treated, and a sealing cup of air permeable, foamed plastics filter material, said cup including an edge portion adapted to form an enclosure around the area to be treated, a window pane opposite said edge portion, and a peripheral wall with a passage for passing a front portion of said nozzle into said enclosure.

5. The device of claim 4, wherein said edge portion is bevelled.

6. The device of claim 4, wherein said window pane extends at an angle with respect to a plane formed by said edge portion.

7. A hand-held device for treating small surface areas with a jet of pressurized air containing sand particles, comprising a compartment for holding a supply of said sand, a piston rearwardly confining said compartment and adapted to be advanced by pressurized air, a feed channel communicating with the front end of said compartment, an inlet opening provided in a wall of said compartment in a region where it communicates with said feed channel, for admitting pressurized air into the compartment for fluidizing the sand, a head portion including a mixing chamber for mixing the sand supplied through said feed channel with pressurized air, a nozzle for blasting the mixture onto the surface area to be treated, and wherein said nozzle and said feed channel have ends which project into said mixing chamber from opposite ends thereof and are laterally displaced from each other, the end of said feed channel projecting beyond the end of said nozzle so that when said device is inoperative and vertically oriented, said feed channel become blocked by sand before sand can reach and flow outwardly through said nozzle.

* * * * *